United States Patent [19]

Musher et al.

[11] 3,939,190
[45] Feb. 17, 1976

[54] GROUP V PENTAVALENT ATOM-CONTAINING COMPOSITIONS

[75] Inventors: Jeremy Musher, New York, N.Y.; Kai Su, Rutherford, N.J.

[73] Assignee: Evelyn Musher, New York, N.Y.

[22] Filed: Feb. 25, 1972

[21] Appl. No.: 229,499

[52] U.S. Cl. ............. 260/446; 260/21 M; 260/2 P; 260/75 R; 260/77.5 AR; 260/7 PR; 260/440; 260/447; 260/606.5 P; 260/606.5 N
[51] Int. Cl.² .................. C07F 9/90; C07F 9/92
[58] Field of Search ................................. 260/446

[56] References Cited
UNITED STATES PATENTS
2,913,428 11/1959 Schoepfle et al. ............... 260/446
3,287,210 11/1966 Leebrick ........................... 260/446

*Primary Examiner*—Arthur P. Demers
*Attorney, Agent, or Firm*—Kenyon & Kenyon Reilly Carr & Chapin

[57] ABSTRACT

A compound having the molecular formula:

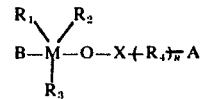

wherein, M is selected from the group consisting of pentavalent atoms of Group V of the Periodic Table; $R_1$, $R_2$ and $R_3$ are selected from the group consisting of substituent groups bondable to M; X is an electron withdrawing group; A is a connecting group capable of undergoing either condensation or addition reactions with compatible function groups of other compounds; $R_4$ is an optional connecting group between the X and A groups; B is selected from the group consisting of $R_1$, $R_2$, $R_3$, $O-X+R_4)_nA$ and $O-X-R_5$, and wherein $R_5$ is selected from the group consisting of $R_1$, $R_2$ and $R_3$; and $n$ is the integer 0 or 1. These pentavalent atom-containing compositions may be reacted into polymers with monomers, prepolymers or polymers. The compositions and polymers have flame-retardant properties.

11 Claims, No Drawings

GROUP V PENTAVALENT ATOM-CONTAINING COMPOSITIONS

Disclosure of the Invention

This invention relates to new compositions of matter containing a pentavalent atom of Group V of the Periodic Table. More particularly, the invention relates to such a composition of matter wherein the pentavalent atom of Group V is covalently bonded in at least 1 and preferably 2 of its valence bonds to atoms selected from the group consisting of oxygen, sulphur and nitrogen which are in turn covalently bonded to an electronegative group. The electro-negative group is chemically connected to a group capable of undergoing a condensation or addition reaction with compatible functional groups of organic compounds. The invention also relates to polymers containing units derived from the described compositions of matter resulting from said condensation or addition reaction. The remaining valence bonds of the pentavalent atom are taken up by organic substituent groups known to be bondable to that atom.

It has been found that the new compositions of matter of this invention possess flame-retardant characteristics. When they are physically admixed with other materials they retard the overall flammable characteristics of the admixture. Furthermore, polymers containing units therein as herein described, and which units contain said pentavalent atom, which is preferably antimony, have been found to retard burning and will not sustain a flame. Polymers have been prepared which are stable in air at temperatures up to 400°C.

The pentavalent atom may be of any of the elements of phosphorus, arsenic, antimony or bismuth. Antimony is preferred because of its superior non-flammable characteristics and the invention herein will be described primarily in terms of pentavalent antimony.

It is well known that Group V oxides, generally of valence 3 (i.e., $As_2O_3$, $Sb_2O_3$, $Bi_2O_3$ and oxy-compounds of phosphorus of valences 3 and 5 such as triphenyl phosphite and tritoly phosphate) are useful as polymer additives in order to reduce the flammability thereof, often in combination with chlorine or bromine. These addition materials are usually toxic to humans. Since they generally are of a low molecular weight, their availability for causing a toxic reaction is greatly enhanced due to their consequently relatively high mobility in the matrix to which they are added, and in the surrounding environment thereof. Furthermore, the addition materials are not chemically combined into the polymeric structure, thus making it difficult to control their action and activity in the sense of preserving the desired physical properties since they may be readily removed from the admixture by vaporization, abrasion, or solvation.

The compounds of the present invention have been found to be extremely stable under atmospheric conditions in both the monomeric and polymeric forms. This is particularly surprising in view of the recognized characteristics of Group V atom-containing compounds, such as pentaethoxyphosphorane, that they are generally not stable under atmospheric conditions. Among the most stable of the known components of such pentavalent atoms are the organic esters of triphenyl antimony oxide having the formula:

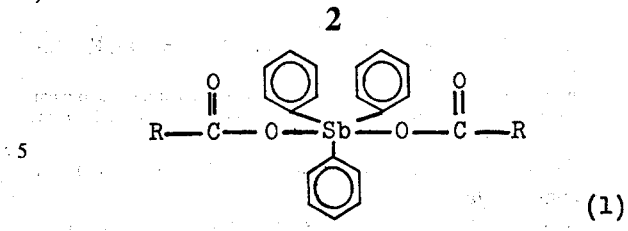

(1)

wherein R is $CH_3$ or $C_6H_5$. However, these compounds have not been found to have any significant utility.

The prior art has described preparations of some polymers of pentavalent atoms of Group V. However, in all cases of which we are aware, the atom, and specifically antimony, was bonded to the organic system through an ether linkage (i.e., M—O—C) with the carbon of the ether being fully saturated, or by means of a direct carbon linkage to the Group V atom (M—C).

The present invention is concerned with the preparation of stable pentavalent atom-containing monomeric molecules with, at least one and preferably two sites which are reactive in the sense that they can react with organic monomers or prepolymers of polyethers, polyesters, polyamides, polyurethanes, polyolefines, and the like, to form copolymers therewith. Also, the pentavalent atom-containing monomeric molecules can react with active sites on polymers as either pendant groups graft polymers or cross-linking groups, or via weakly bonded interactions as through hydrogen bonds. The present invention is also concerned with the methods of reacting these monomers with the organic monomers, prepolymers or polymers in various proportions to form the copolymers, cross-linked polymers or graft polymers. Furthermore, the present invention includes the copolymers, cross-linked polymers or graft polymers so formed. These copolymers or interpolymers are useful particularly for their flame-retardant properties, which are believed to be attributable to the presence of the Group V atom in the polymer.

The advantage of using the hypervalent Group V atoms lies in the fact that the neutral atom valence can expand no further than five, and hence these molecules are less reactive than their lower valence counterparts.

In accordance with the present invention there is prepared a new compound having the molecular formula*:

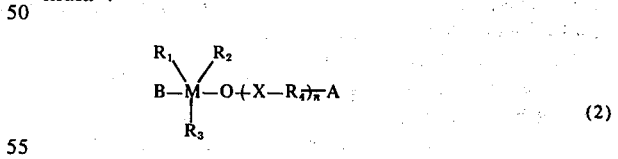

(2)

wherein, M is selected from the group consisting of pentavalent atoms of Group V of the Periodic Table; $R_1$, $R_2$ and $R_3$ are selected from the group consisting of substituent groups bondable to M; X is an electron withdrawing group; A is a connecting group capable of undergoing either condensation or addition reactions with compatible function groups of other compounds; $R_4$ is an optional connecting group between the X and A groups; B is selected from the group consisting of $R_1$, $R_2$, $R_3$, O-X-$(R_4)_n$ A and O-X-$R_5$, and wherein $R_5$ is selected from the group consisting of $R_1$, $R_2$ and $R_3$; and $n$ is the integer 0 or 1.

*Throughout this specification, the same symbols are intended to mean the same thing. Throughout this specification "O" in a formula means oxygen.

Throughout this specification "O" in a formula means oxygen.

More particularly, M is selected from phosphorus, arsenic, antimony and bismuth.

$R_1$, $R_2$, $R_3$ may be the same or different and are selected from an aromatic or aliphatic group. More specifically, these groups may be aryl and substituted aryl including halogenated and oxyaryl groups, and alkyl and substituted alkyl including halogenated and oxyalkyl groups. Generally speaking, the preferred aryl and substituted aryl groups are phenyl or naphthyl, and the preferred alkyl groups are lower alkyl such as $C_1$ - $C_6$. The halogens described above include fluorine, chlorine, bromine and iodine.

The electron withdrawing X group may be any of the following:

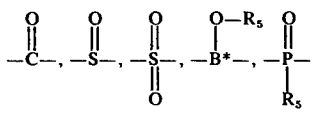

*Boron

The carbonyl group is preferred since it is believed to be easiest to work with and is useful in retaining the organic character of the compound and/or polymer. An electron withdrawing group is a group of atoms whose affinity for electrons or electronegativity, is greater than that for the average group, generally taken to be a hydrocarbon. While oxygen, which is bonded directly to M, is itself electron withdrawing, and hence apparently able to stabilize hypervalent bonds, it can do so only weakly and the products are usually sensitive to the moisture in the air. The added stability imparted by the electron withdrawing group X is of critical importance for the utility of these materials.

The connecting group A may be any of: —COOH, —COCl, —SO$_3$H, —NCO, —NH$_2$, —OH, —CH=CH$_2$, and —COOR$_6$ wherein $R_6$ is a lower alkyl, from $C_1$ through $C_5$.

$R_4$ is an optional group which when present in the compound described above, is used to chemically connect the electron withdrawing X group with the connecting A group. It may be any of $R_1$, $R_2$ and $R_3$, but in the divalent form thereof. In other words, the arylene and alkylene form of the group.

"n" is the integer 0 or 1.

The electro-negative group is of importance in that it strengthens the hypervalent bonds so that for example the organic ester of antimony of the formula:

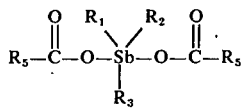
(3)

is far more stable than the organic ether of antimony with linkage:

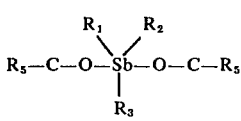
(4)

The latter, ether, is generally unstable in atmospheric moisture at room temperature, whereas the former, ester, is stable in hot water. The polymers formed using the ester structure as described are stable in air even when heated up to 400°C.

The monomeric compounds do not burn until they have been exposed to a flame over a long period of time. The flame-retardant properties are gradually affected by prolonged exposure to heat, which may possibly be due to vaporization of the metal atom. An advantage of incorporating the metal atom into the organic system rather than using simply the oxide is that such vaporization will only occur at greatly increased temperatures and only after longer exposure to such temperatures. A further advantage is that the flame-retardant properties cannot be washed out or rubbed out in normal use of the polymer.

The properties of the polymeric materials are such that they are self-extinguishing in the atmosphere and will only sustain a flame in heavily oxygen-rich atmospheres as attainable generally only in the laboratory. The critical concentration of metal atoms varies from polymer to polymer and it appears that even with concentrations as small as one metal atom per 200 carbon atoms the materials will not sustain a flame.

We have prepared the monomeric compounds of this invention according to the reactions:

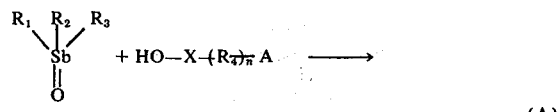

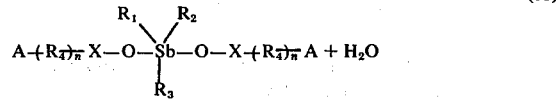
(A)

and

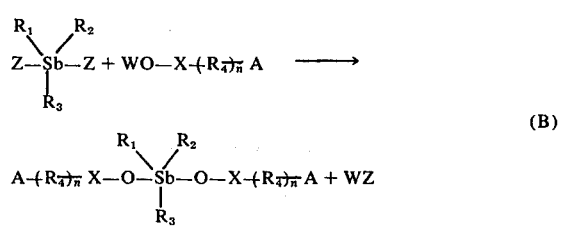
(B)

wherein Z is a halogen, and W is silver, sodium or a silyl group such as $(CH_3)_3Si$.

These reactions may be carried out either in an inert solvent or in the melt. The desired tri-substituted antimony oxide. e.g., $(C_6H_3)_3SbO$, is reacted with an excess of a bifunctional reagent, such as terephthalic acid by refluxing in a suitable solvent for several hours. This insoluble product is collected after cooling and purified using standard techniques. The reaction can also be carried out directly in a melt, e.g., by adding $(C_6H_5)_3SbO$ to a melt of excess adipic acid at 150°C. The cooled solid is washed until unreacted starting materials are eliminated and the product is purified using standard techniques. The new compounds can be characterized completely by infra-red, nuclear-magnetic resonance, mass-spectroscopy and elemental analysis, as desired.

Examples of the pentavalent atom-containing monomeric compounds of this invention are set forth herein.

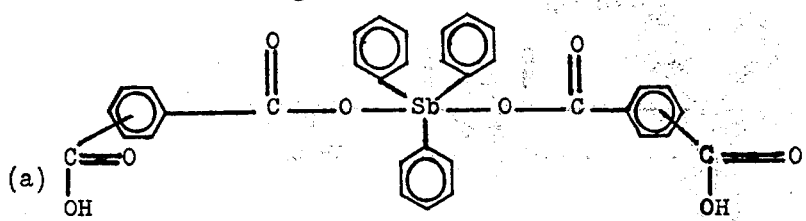
(a) Triphenylantimony di-phthalic acid ester
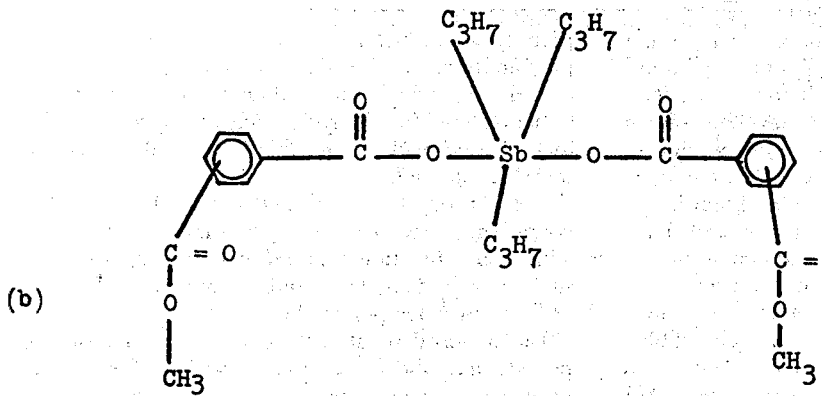
(b) Tri-n-propylantimony di(methylphthalate)
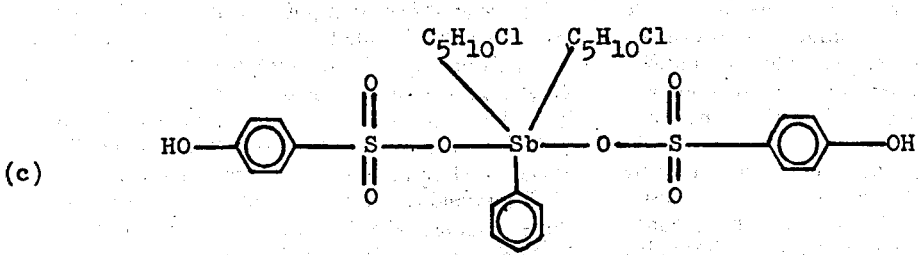
(c) Phenyl-di(1-chloro-n-pentyl)antimony (di(p-hydroxy-benzosulfonate)
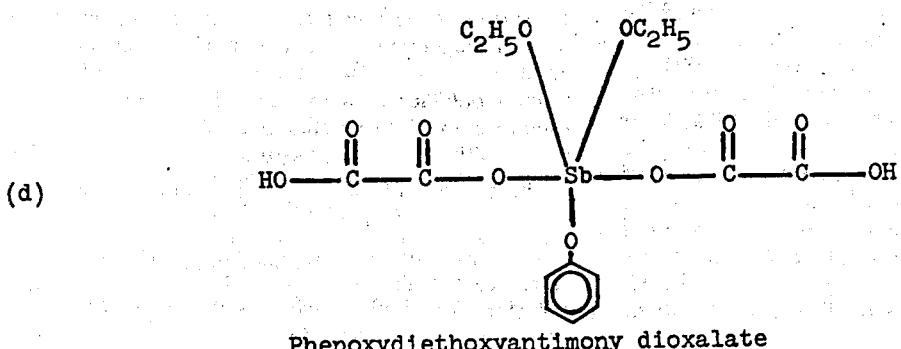
(d) Phenoxydiethoxyantimony dioxalate
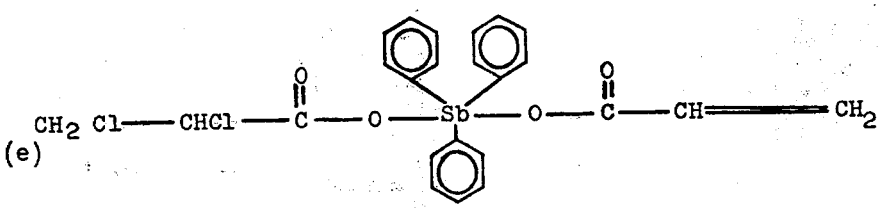
(e) Triphenylantimony dichloroacrylate acrylate ester
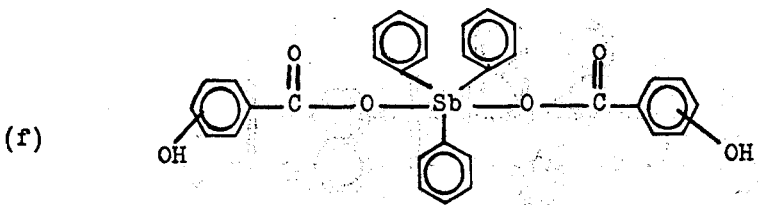
(f) Triphenylantimony di-hydroxybenzoate (g)
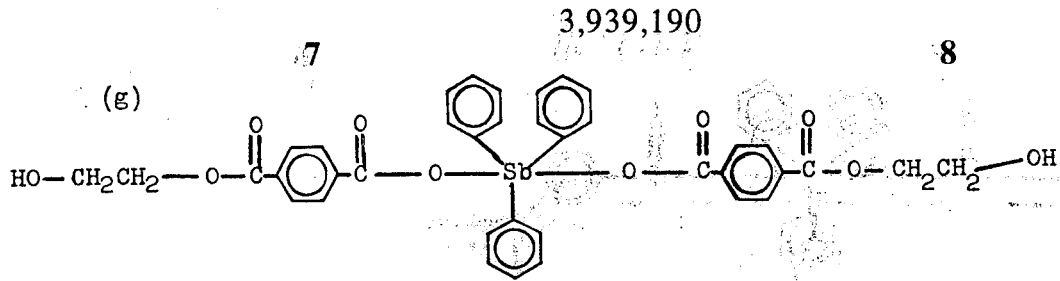

Triphenylantimony di(phthalate ethylene glycol ester)

Other compounds which are included within the scope of this invention include those pentavalent atom-containing monomeric compounds which are described in terms of the generic molecular formula shown above. At the present time, compounds (a), above, namely, triphenyl antimony diterephthalic acid and (f) triphenyl antimony di-p-hydroxybenzoate, specifically, are the preferred compounds. These compounds have been found to be useful as flame-retardant agents in their own right and as suitable monomers for polymerization reactions with other monomers or prepolymers or polymers which have functional groups compatible with the terminal carboxylic acid (or equivalent acetyl halide and hydroxyl groups of these compounds. For example, hydroxy terminated compounds such as ethylene glycol, or hydroxy terminated esters such as the ethylene glycol-terephthalic acid adduct, or isocyanate terminated adducts may be reacted with the pentavalent atom-containing monomeric compound in order to yield polyesters or polyurethanes having the pentavalent atom in the polymer chain.

Also preferred are the pentavalent atom-containing monomeric compounds which have terminal ester groups which readily undergo an ester interchange reaction, such as the reaction of triphenyl antimony methyl terephthalate with a hydroxy terminated ester prepolymer to yield a polyester.

In addition to preparing the polyesters described above, pentavalent atom-containing monomeric compounds may be prepared which contain terminal hydroxy groups either directly as part of the A connecting group, or by means of a pre-reaction of the acid- or ester- terminated pentavalent atom-containing monomeric compound with a difunctional compound of which at least one functional group is hydroxy, and the other is reactable with said terminal acid or ester group. These hydroxy terminated pentavalent atom-containing monomeric compounds may then be reacted with diisocyanate compounds to form urethane prepolymers, which in turn may be further reacted with polyfunctional hydroxy- and/or amine-containing compounds to produce polyurethanes. Also polyether and polyester urethanes may be made in this manner. They may also be made in the form of a foam by conventional techniques.

The carboxylic acid terminated pentavalent atom-containing monomeric compound may also be reacted with a polyfunctional amine terminated compound, such as the diethylene amine-adipic and adduct in order to produce polyamides, such as nylons.

The pentavalent atom-containing monomeric compounds may also be terminated with olefinic or vinyl groups which may be reacted with other vinyl groups of other monomers or polymers.

The desired vinyl compound containing the pentavalent atom can be made by condensation of the antimony oxide, e.g., $(C_6H_5)_3SbO$, with the corresponding vinyl acid, e.g., acrylic acid in a hot solvent for about one hour. The excess acid is removed by vacuum and the product is purified by recrystallization. This bifunctional vinyl compound is used in making cross-linked polymers and it is also used after partial reduction or partial halogenation to the mono-vinyl derivative in making noncross-linked polymers.

The following examples are illustrative of the invention. All of the monomeric products are analyzed by the various modern spectroscopic methods of infra-red, nuclear magnetic resonance and mass-spectrometry in addition to chemical analysis. The washed and extracted polymer materials are analyzed by intra-red spectroscopy and elemental analysis.

EXAMPLE 1

Preparation of Monomer - Triphenyl Antimony Dimethylterephthalate

Triphenyl antimony oxide and dimethylterephthalate were reacted to yield triphenyl antimony dimethylterephthalate.

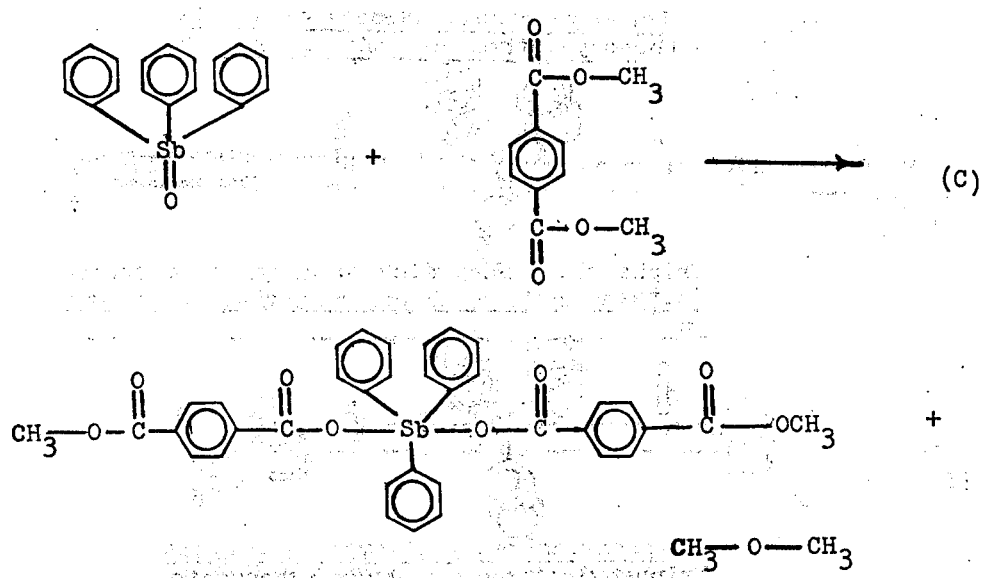

EXAMPLE 2

Preparation of Monomer - Triphenyl Antimony DiTerephthalic Acid

Triphenyl antimony oxide was reacted with terephthalic acid to yield triphenyl diterephthalic acid.

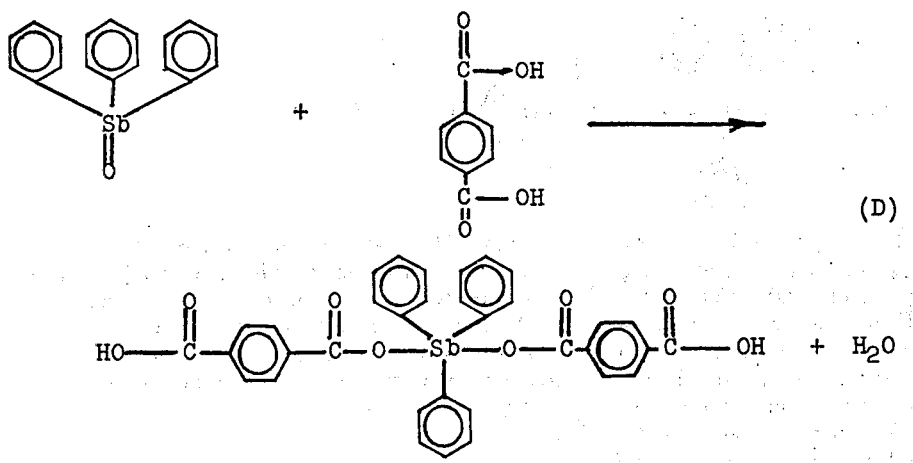

(D)

EXAMPLE 3

Preparation of Monomer - Triphenyl Antimony Disalicylate

Triphenyl antimony oxide was reacted with o-hydroxy benzoic acid (salicylic acid) to yield triphenyl antimony di(hydroxy benzoic acid) (or triphenyl antimony disalicylate).

Triphenyl antimony oxide (3.7 g.; 0.001 mole) and salicylic acid 3.0.; 0.0021 mole) were suspended in benzene (100 ml.) and the reaction was permitted to proceed. The reaction was carried out at 60°–70°C. until a clear solution was obtained. The benzene was removed by vacuum distillation. The oily residue was dissolved in ethyl acetate (50 ml.). The ethyl acetate solution was extracted with an aqueous 10% sodium bicarbonate solution (50 ml.) followed by washing with (50 ml.) water. The ethyl acetate solution was dried over anhydrous magnesium sulfate. A white powder was collected after removing ethyl acetate by vacuum distillation. The white powder was recrystallized from hot benzene and yielded 5.4 g. The material was self-extinguishing as observed by performing qualitative burning tests in Bunsen burner flames in the laboratory.

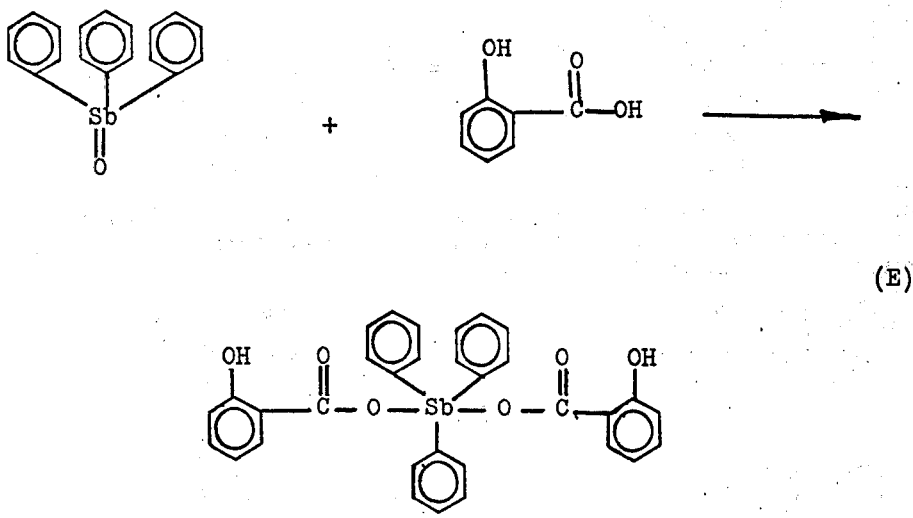

(E)

EXAMPLE 4

Preparation of Monomer - Triphenyl Antimony Di(p-hydroxybenzoate

Triphenyl antimony oxide was reacted with p-hydroxybenzoic acid to yield triphenyl antimony di(p-hydroxybenzoate).

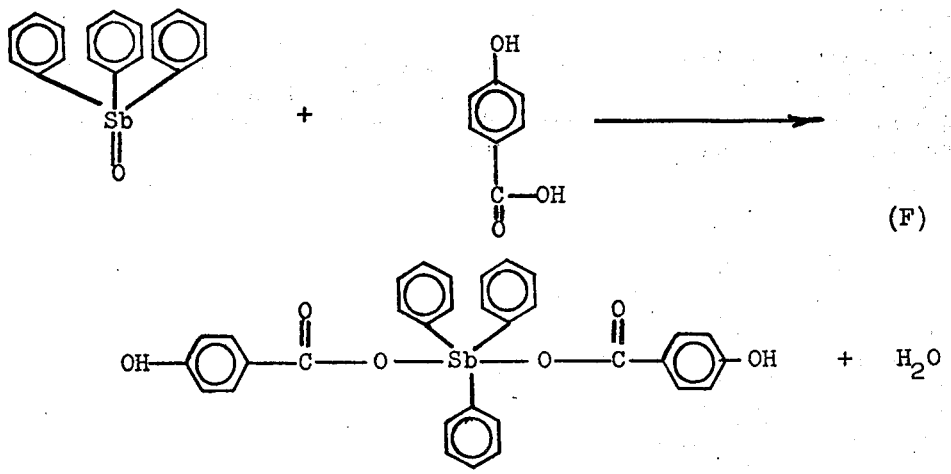

(F)

Triphenyl antimony oxide (3.7 g.; 0.001 mole) was added to a solution of p-hydroxybenzoic acid (3.0 g.; 0.0021 mole) in acetophenone (100 ml.). The mixture was heated to 100°–110°C. until a clear solution was obtained. The solution was then cooled to room temperature and a white powder material was obtained. It was recrystallized from hot acetophenone to give a white crystalline material. The material was self-extinguishing as observed by performing qualitative burning tests in Bunsen burner flames in the laboratory.

EXAMPLE 5
Preparation of Monomer - Triphenyl Antimony Diacrylate

Triphenyl antimony oxide was reacted with acrylic acid to yield triphenyl antimony diacrylate.

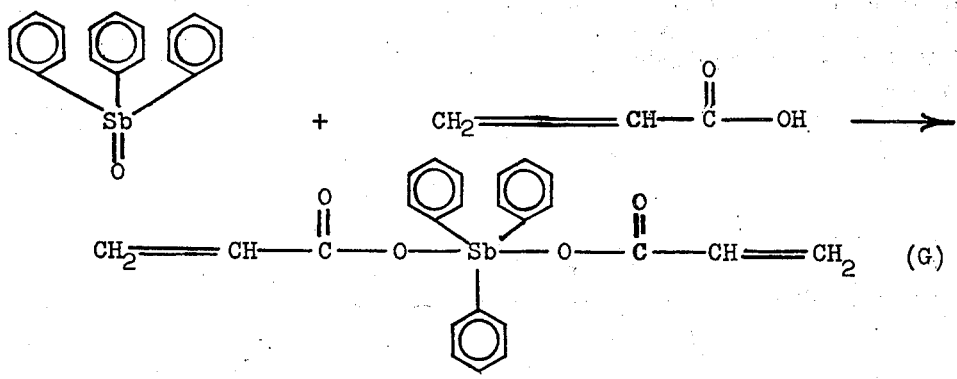

(G)

Triphenyl antimony oxide (3.7 g.; 0.001 mole) was added to acrylic acid (15 ml.). The reaction mixture was kept at 95°C. for an hour with good stirring. The excess acrylic acid was removed by vacuum. The viscous residue was soon crystallized upon adding hexane. It was recrystallized from hot benzenehexane to give white crystals. Yield 5 g. (91%). The material was self-extinguishing as observed by performing qualitative burning tests in Bunsen burner flames in the laboratory.

EXAMPLE 6
Preparation of Monofunctional Monomer - Triphenyl Methyl Antimony Iodide Triphenyl antimony was reacted with methyliodide to yield triphenyl methyl antimony iodide. This was in turn reacted with the silver salt of acrylic acid to yield triphenyl methyl antimony acrylate. The material was self-extinguishing as observed by performing qualitative burning tests in Bunsen burner flames in the laboratory.

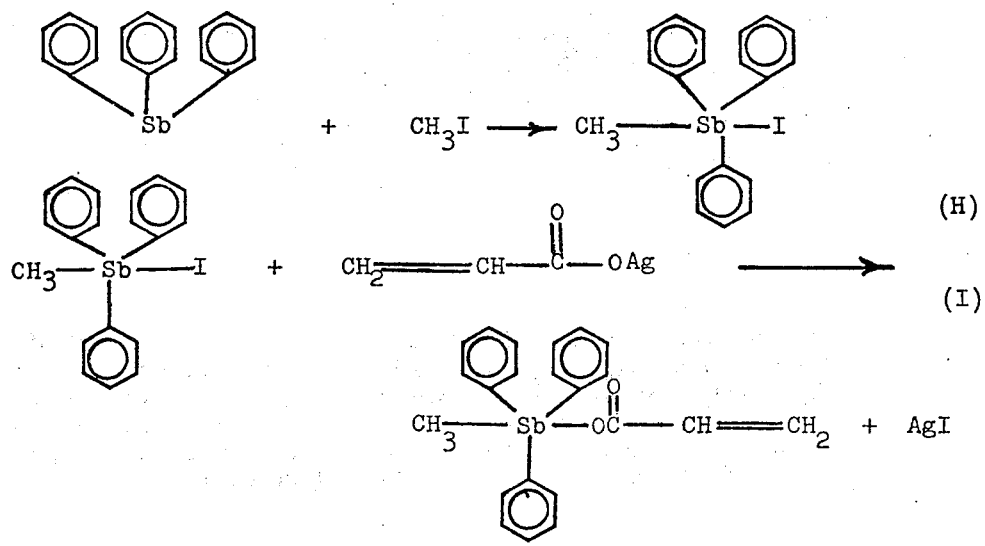

EXAMPLE 7

Polymerization of Monomers of Example 1

The dimethyl ester was reacted with excess ethylene glycol and dimethylterephthalate to yield a polyester, namely, polyethylene terephthalate-triphenyl antimony di(methyl terephthlate) copolymer.

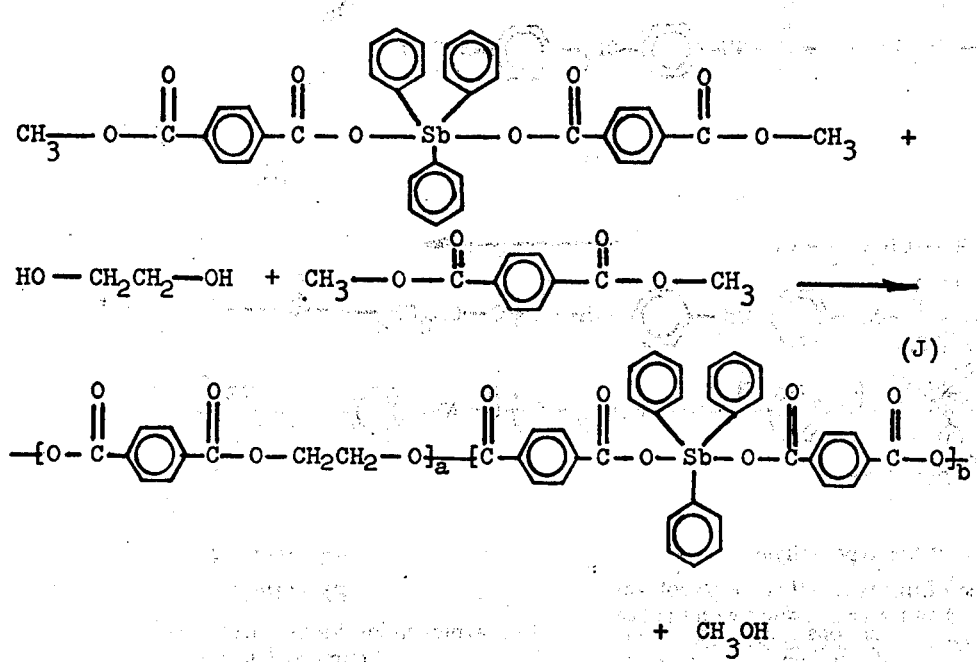

(J)

Polymerization was carried out by adding the triphenylantimony oxide to the melted dimethyl terephthalate at 197°C. Ethylene glycol was then added by following the conventional polymerization procedure. (See i.e., Sorenson and Campbell "Preparative Methods of Polymer Chemistry" ppg. 131–132 (1968 Interscience New York).

The material was thoroughly washed and purified to remove all monomeric materials. The resultant polymer was identified as that shown in equation (J), by IR and elemental analysis. The proportion of $a$ groups was at least 200 times the number $b$ groups.

The polymer exhibited fire-retardant properties. The material was self-extinguishing as observed by performing qualitative burning tests in Bunsen burner flames in the laboratory.

EXAMPLE 8

Polymerization of Monomers of Example 2

The diacid monomer of Example 2 was reacted with excess ethylene glycol to form an hydroxyl terminated polyester prepolymer. This in turn was reacted with methylene bis-(phenyl isocyanate) to form a co-prepolymer of the hydroxyl terminated polyester and the diisocyanate. The prepolymer was then reacted with ethylene glycol to yield a urethane polymer. The material was self-extinguishing as observed by performing qualitative burning tests in Bunsen burner flames in the laboratory.

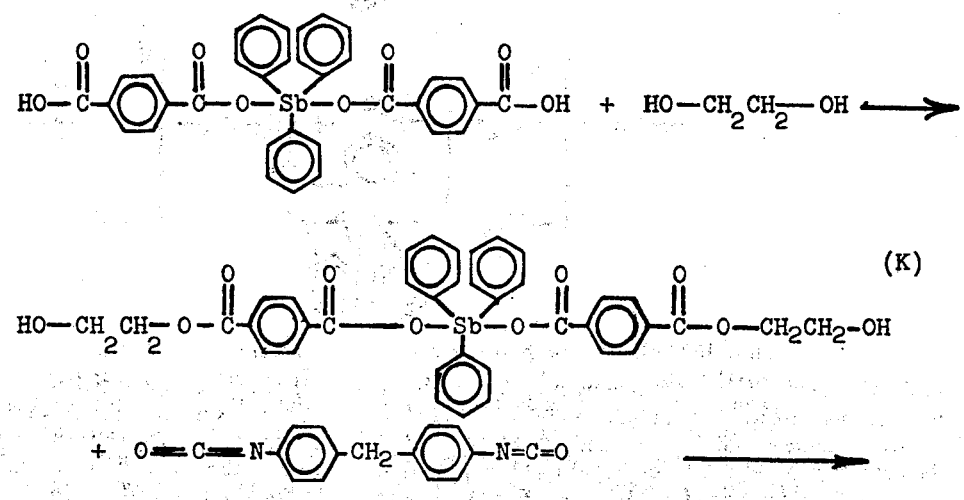

(K)

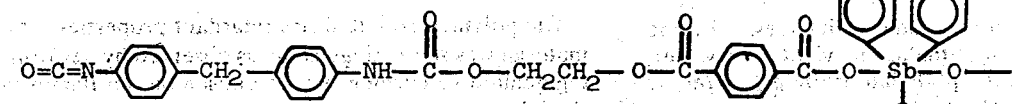

(L)

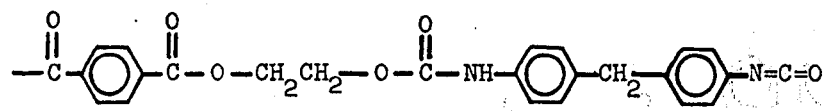

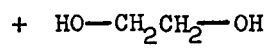

(M)

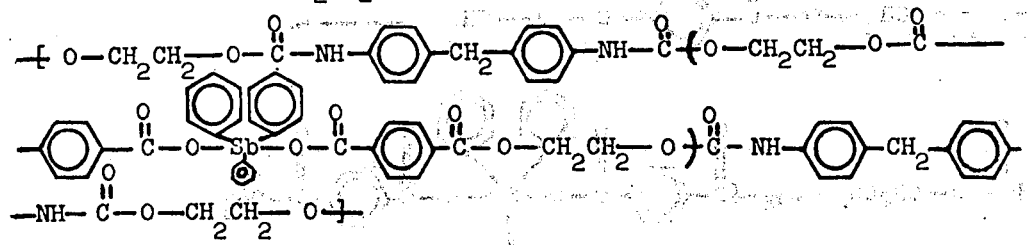

In another example of this type, ethylene glycol was replaced by ethylene diamine and reacted with the last mentioned prepolymer to form a urea polymer.

All of the conventional reactions known in the art which can be carried out with urethane-type polymers may be carried out with the above-referred to urethane polymers. For example, cross-linking may be accomplished by reaction of the antimony prepolymer with a trifunctional hydroxyl compound such as glycerol or trihydroxytoluene and then proceeding as shown. Also, the active hydrogen on the chain nitrogen may be used as a cross-linking or pendant group site. For example as in the reaction of the -NH- group with formaldehyde.

EXAMPLE 9

Copolymerization Methyl Methacrylate-Triphenyl Antimony Diacrylate

Triphenyl antimony diacrylate was reacted with methyl methacrylate to yield a partially cross-linked polymer.

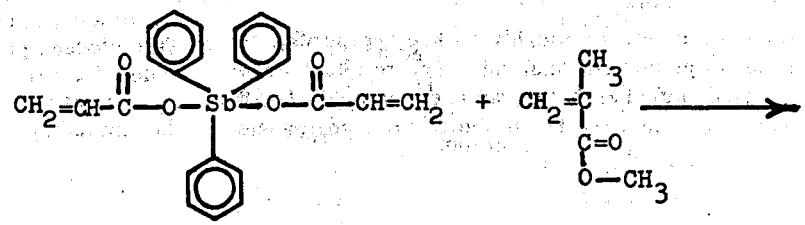

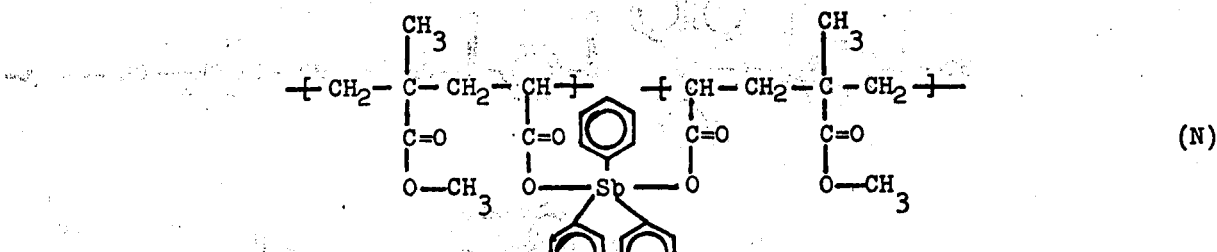

(N)

Freshly recrystallized triphenyl antimony diacrylate (2 g.) was dissolved in freshly distilled methyl methacrylate (15 g.). The mixture was poured into a polymerization tube and $\alpha,\alpha'$ azodiisobutyronitrile catalyst (0.01 g.) was added. The mixture was purged with nitrogen and sealed under vacuum. The mixture was maintained in a constant temperature bath at about 55°C. for 12 hours. A clear solid polymer was formed. Preliminary results show this polymer to be self-extinguishing. The material was self-extinguishing as observed by performing qualitative burning tests in Bunsen burner flames in the laboratory.

methacrylate to yield a copolymer. The material was self-extinguishing as observed by performing qualitative burning tests in Bunsen burner flames in the laboratory.

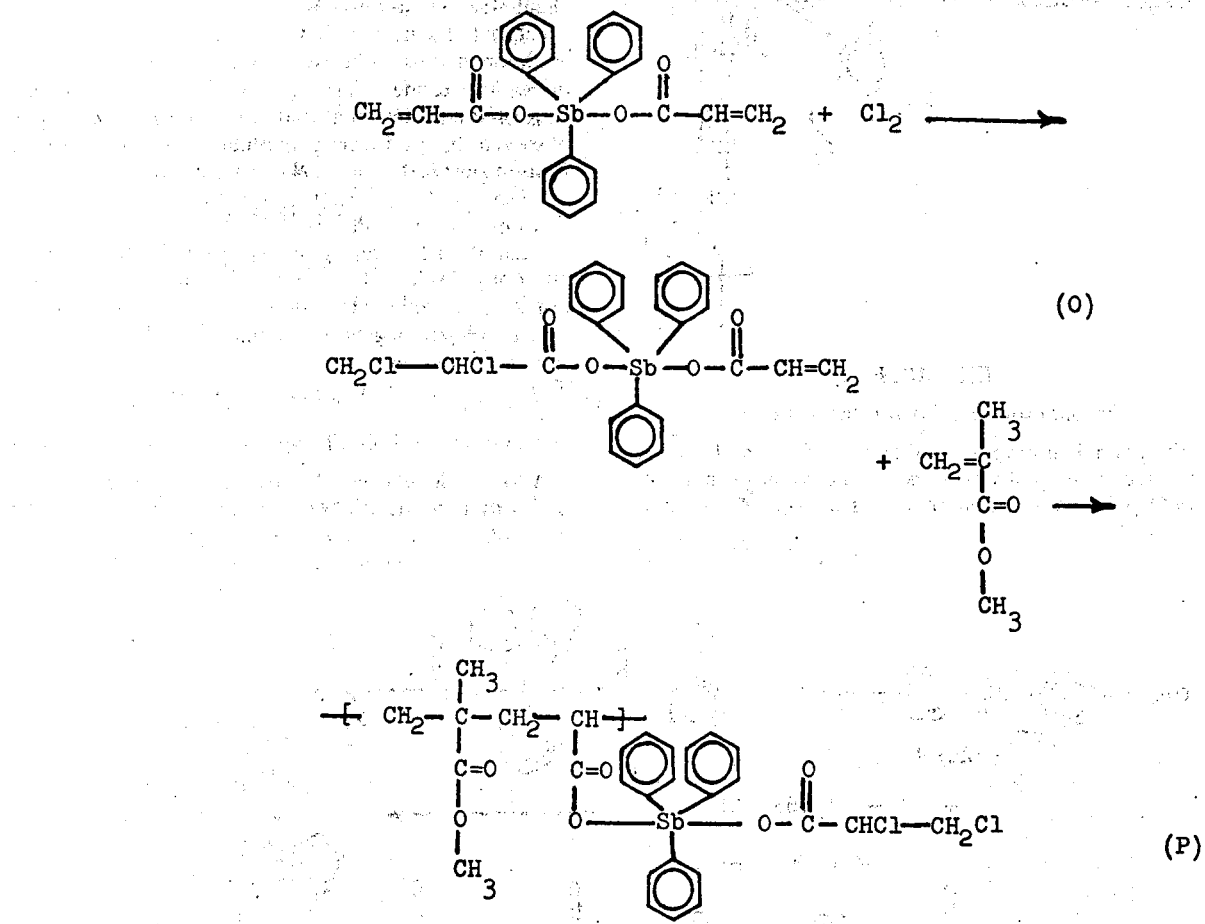

EXAMPLE 10

Copolymerization of Methyl Methacrylate - Triphenyl Ethyldichloro- Antimony Acrylate The triphenyl antimony diacrylate of Example 5 was partially chlorinated with chlorine gas to saturate one of the olefinic groups of the acrylate moiety. This compound was then reacted, as in Example 9, with methyl

EXAMPLE 11

The partially chlorinated triphenyl antimony diacrylate of Example 10 was oxidized with peracetic acid and the resultant epoxide was copolymerized with propylene oxide in the presence of an initiator to give the resultant antimony-containing polyether. The resultant material was washed and shows the self-extinguishing properties. The material was self-extinguishing as observed by performing qualitative burning tests in Bunsen burner flames in the laboratory.

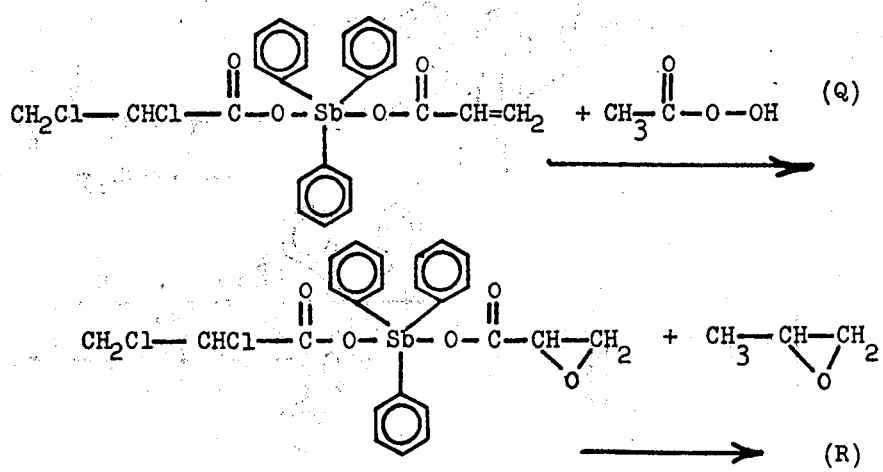

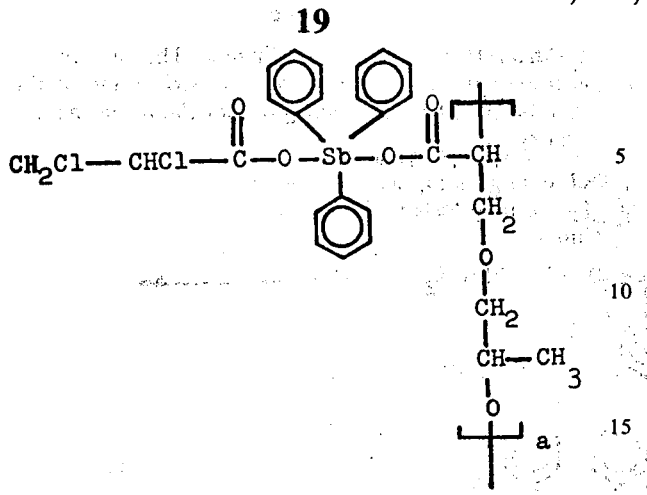

EXAMPLE 12

Preparation of a Polyurethane Polymer

Triphenyl antimony disalicylate of Example 3 was reacted with methylene bis (4-phenyl isocyanate) to yield poly-[ethylene methylene bis (4-phenyl carbonate)].

from moisture. To this rapidly stirred suspension is added triphenyl antimony disalicylate (0.63 g.) and ethylene glycol (0.558 g.) in dimethylsulfoxide (5 ml.). The reaction is heated at 115°C. for 1½ hours. The clear, viscous solution is then poured into water to precipitate the polyurethane. The tough, white polymer is chopped up in a blender, washed with water, then dried in a vacuum oven at 90°C. The material is self-extinguishing. The material was self-extinguishing as observed by performing qualitative burning tests in Bunsen burner flames in the laboratory.

EXAMPLE 13

Example 12 is repeated, except that the triphenyl antimony disalicylate is replaced with equal mole proportions of triphenyl antimony di-p-hydroxybenzoate. The corresponding polyurethane is produced and it is self-extinguishing.

EXAMPLE 14

Preparation of Poly (Triphenyl Antimony Sebacate)

A low molecular weight antimony polyester was prepared by reacting triphenyl antimony oxide with sebacic acid. It may be used as a plasticizer for other poly-

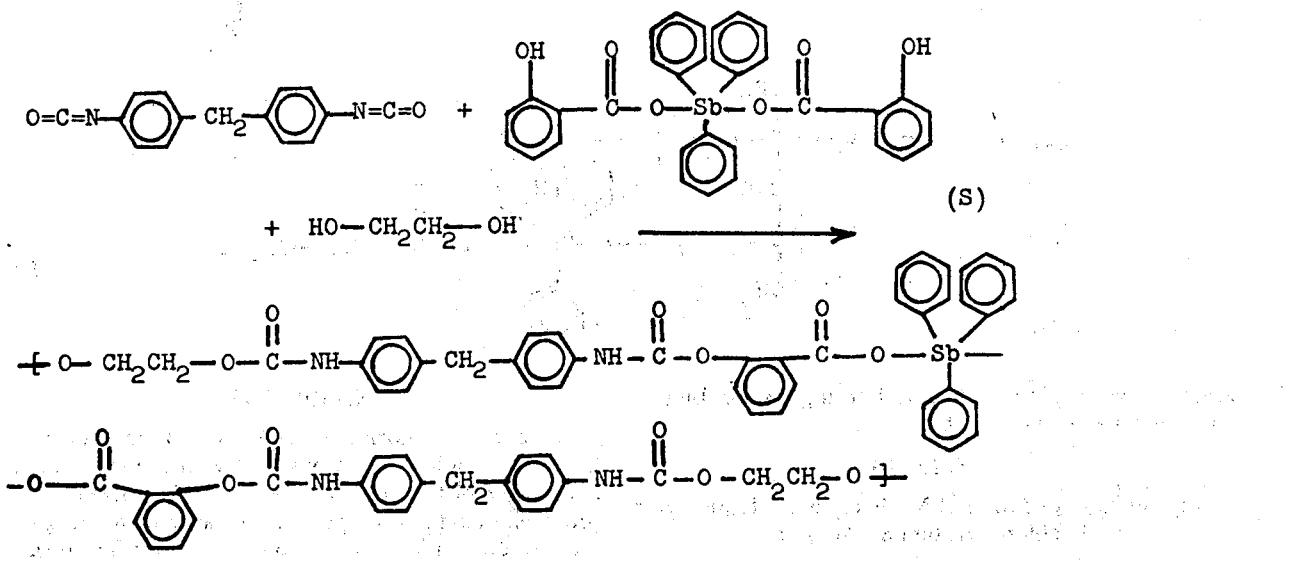

4-Methyl pentanone-2 solvent (5 ml.) and (2.502 g.) is placed in a three-necked round bottom flask equipped with stirrer and condenser and protected mers such as vinyl polymers, such as polyvinyl chloride, polyvinylidene chloride, copolymers thereof, and the like.

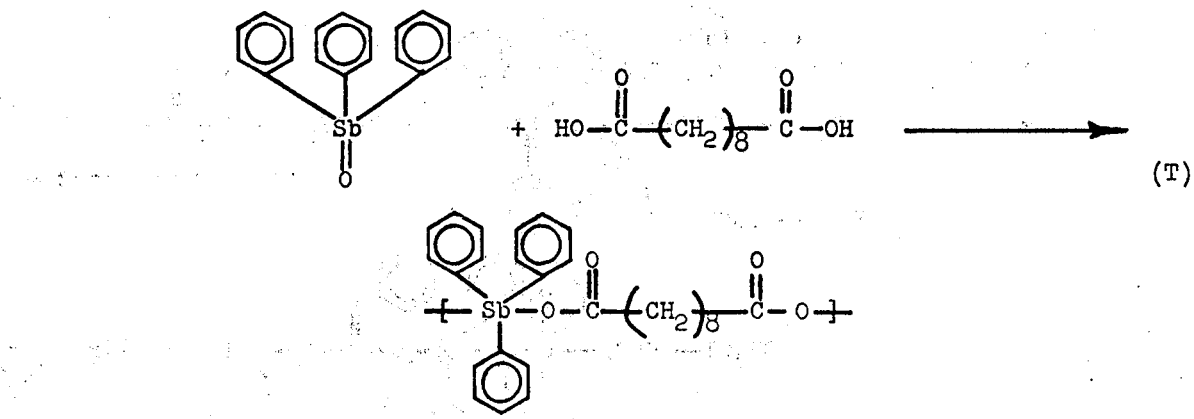

A mixture of sebacic acid (2.02 g.) and triphenyl antimony oxide (3.69 g.) was mixed into benzene (100 ml.) and refluxed for 3 hours in a 250 ml. round bottom flask equipped with a Dean-Stark trap for azeotropic removal of water. To the clear viscous solution was added hexane and a white powder was precipitated. This polymer is soluble in hot benzene, can be drawn into a fiber and poured into a film in the melted state, and will not sustain a flame. The relatively low glass-transition point of the polyester polymer makes it suitable for use as a fire-retardant polymer plasticizer. The material was self-extinguishing as observed by performing qualitative burning tests in Bunsen burner flames in the laboratory.

It will be understood that it is intended to cover all changes and modifications of the examples of the invention herein chosen for the purpose of illustration which do not constitute departures from the spirit and scope of the invention.

We claim:

1. A polymerisable compound having the molecular formula

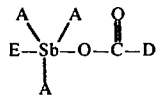

wherein:
   a. A is a phenyl moiety or a lower alkyl moiety up to $C_5$,
   b. D is selected from the group consisting of

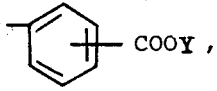

wherein Y is selected from the group consisting of H, —CH$_3$ and —CH$_2$CH$_2$OH,

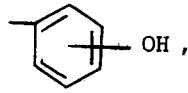

—CH=CH$_2$
and —CHCl—CH$_2$Cl; and
   c. and E is any of D herein or —CH$_3$.

2. The compounds of claim 1 being selected from the group consisting of triphenylantimony di-phthalic acids.

3. The compounds of claim 1 being selected from the group consisting of tri-n-propylantimony di(methylphthalates).

4. The compounds of claim 1 being selected from the group consisting of triphenylantimony di-hydroxybenzoates.

5. The compounds of claim 2 being triphenylantimony di-terephthalic acid.

6. The compounds of claim 1 being triphenylantimony dichloroacrylate acrylate ester.

7. The compounds of claim 4 being triphenylantimony di-parahydroxybenzoate.

8. The compounds of claim 1 being triphenylantimony diterephthalate ethylene glycol ester).

9. The compounds of claim 1 being triphenylantimony dimethylterephthalate.

10. The compounds of claim 4 being triphenylantimony di(orthohydroxy benzoic acid).

11. The compounds of claim 1 being triphenyl methyl antimony acrylate.

* * * * *